United States Patent [19]

Agar

[11] 4,217,774
[45] Aug. 19, 1980

[54] APPARATUS FOR MEASURING THE VALUE OF A FLUID VARIABLE

[76] Inventor: Joram Agar, 2320 Blalock Rd., Houston, Tex. 77080

[21] Appl. No.: 1,041

[22] Filed: Jan. 4, 1979

[51] Int. Cl.³ .............................................. G01N 9/00
[52] U.S. Cl. ................................................... 73/32 A
[58] Field of Search ...................................... 73/32 A

[56] References Cited

U.S. PATENT DOCUMENTS

| 2,943,476 | 7/1960 | Bernstein | 73/32 A |
| 3,298,221 | 1/1967 | Miller et al. | 73/32 A X |
| 3,444,723 | 5/1969 | Wakefield | 73/32 A |
| 3,456,491 | 7/1969 | Brockhaus | 73/32 A |
| 3,585,843 | 6/1971 | Stansfeld | 73/32 A |
| 3,729,982 | 5/1973 | Senda | 73/32 A |
| 3,955,401 | 5/1976 | Catherall | 73/32 A |

FOREIGN PATENT DOCUMENTS

| 4326012 | 10/1965 | Japan | 73/32 A |
| 4418530 | 3/1966 | Japan | 73/32 A |
| 400838 | 4/1974 | U.S.S.R. | 73/32 A |

*Primary Examiner*—Gerald Goldberg
*Assistant Examiner*—Joseph W. Roskos
*Attorney, Agent, or Firm*—Beveridge, De Grandi, Kline & Lunsford

[57] ABSTRACT

Apparatus for measuring the value of a fluid variable comprises a vibrator tube through which the fluid may be passed and which is mounted for clamped-clamped flexural vibration in a holding structure whose stiffness is at least 40% greater than that of the vibratory tube. A driving coil is carried by the holding structure and is arranged in operation to produce the clamped-clamped flexural vibration of the vibratory tube. A pick-up coil is arranged in operation to respond to vibration of the vibratory tube. A support supports the holding structure and the vibratory tube by way of an isolator which substantially prevent transmission of vibration between the support on the one hand and the holding structure and vibratory tube on the other hand.

26 Claims, 4 Drawing Figures

APPARATUS FOR MEASURING THE VALUE OF A FLUID VARIABLE

FIELD OF THE INVENTION

This invention concerns an apparatus for measuring the value of a fluid variable such, for example, as the density of a liquid or of a gas. The apparatus of the present invention is, however, also applicable to the measurement of the value of other fluid variables such as viscosity and pressure.

BACKGROUND OF THE INVENTION

Previously known density meters have frequently employed a vibratory tube through which the fluid whose density is to be measured is passed. The vibratory tube has been arranged to vibrate in the circumferential mode of vibration, also known as the bell mode or the hoop mode, and the value of the vibrations has been used to determine the value of the density of the fluid. Such density meters, however, are limited to use on low viscosity fluids, e.g. fluids having viscosities below 20 cS. Vibratory tubes which are arranged to vibrate in the circumferential mode of vibration, moreover, are expensive to make since their manufacture involves precision machining.

Density meters are also known whose vibratory tubes are arranged to vibrate in the clamped-clamped flexural mode of vibration in which the fluid viscosity has very little damping effect on the vibration. However, in previously known density meters employing vibratory tubes which vibrate in the clamped-clamped flexural mode of vibration, complicated structures have been used to balance the reactions at the nodes of the vibratory tubes. Thus in one construction, shown in British Patent Specification No. 1,158,790, this balancing is effected by the use of twin vibratory tubes which communicate with each other adjacent the nodes and which need to match each other extremely closely if the meter is to operate satisfactorily.

In another construction, shown in British Patent Specification No. 1,432,165, only one single vibratory tube is employed, but a mass is connected to the vibratory tube at each node thereof by way of a cantilever system which balances the reaction at the respective node. Such a construction, however, involves complicated matching at one frequency only.

SUMMARY OF THE INVENTION

According therefore to the present invention, there is provided apparatus for measuring the value of a fluid variable comprising a vibratory tube through which the fluid may be passed and which is mounted for clamped-clamped flexural vibration in a holding structure whose stiffness is at least 40% greater than that of the vibratory tube; driving means carried by said holding structure and arranged in operation to produce the said clamped-clamped flexural vibration of the vibratory tube; pick-up means arranged in operation to respond to vibration of the vibratory tube; and a support which supports the holding structure and vibratory tube by way of isolator means which substantially prevent transmission of vibration between the support on the one hand and the holding structure and vibratory tube on the other hand.

Thus the present invention provides a simple, and therefore inexpensive, apparatus for accurately measuring the value of the density, or some other variable, of a fluid by means which do not require precision machining of a vibratory tube and which do not require complicated structure to balance the reactions at the nodes.

Preferably, the pick-up means is also carried by the holding structure.

Both the vibratory tube and the holding structure may be connected to the said support by way of respective isolator means.

There may be tension producing means for producing axial tension of the vibratory tube.

In one embodiment of the present invention, the tension producing means comprises a piston and cylinder arrangement, means being provided for supplying the cylinder with the said fluid. Thus the piston may be secured to the holding structure and may be slidably mounted within a cylinder whose interior communicates with the interior of the vibratory tube.

In another embodiment of the present invention, the isolator means comprises a bellows, and means may be provided for supplying the interior of the bellows with the said fluid. Thus the bellows may be interposed between the holding structure and the support, the interior of the bellows communicating with the interior of the vibratory tube.

In yet another embodiment of the present invention, the isolator means comprise shock absorbers interposed between the holding structure and the support.

The holding structure may comprise two spaced frame members which are rigidly secured to the vibratory tube, and a plurality of interconnector members which extend between and are rigidly secured to or are integral with the frame members.

The stiffness of each interconnector member may be at least twice, and indeed may be 10 times or more, that of the vibratory tube.

Compensating means may be provided which compensate for the effect of temperature on the value of the said fluid variable.

Thus the compensating means may comprise means for passing the said fluid in heat exchange relationship with the holding structure so that there is substantially no temperature differential between the holding structure and the vibratory tube. Thus the said fluid may be passed in heat exchange relationship with said interconnector members.

Each interconnector member, moreover, may be a tubular member, while the vibratory tube may be constituted by one portion of a tube which is rigidly secured to and extends between the said frame members, the said tube having further portions thereof each of which extends through and is in heat exchange relationship with a respective tubular member.

The compensating means may comprise temperature responsive means for measuring the temperature of the fluid, the pick-up means being connected to a meter whose reading is adjusted by the temperature responsive means.

Alternatively, the interconnector members may be made of a material having a higher coefficient of thermal expansion than that of the vibratory tube.

Means may be provided for subjecting both the interior and the exterior of the vibratory tube to the pressure of the said fluid.

The support may comprise a sealed enclosure within which the holding structure and vibratory tube are mounted. This sealed enclosure may contain dry air or an inert gas, or may be evacuated.

The driving means may be an electro-magnetic driving means, and the vibratory tube, which may be made of non-magnetic material, may carry a magnetisable member disposed adjacent to the electro-magnetic driving means.

DESCRIPTION OF THE DRAWINGS

The invention is illustrated, merely by way of example, in the accompanying diagrammatic drawings, in which.

DESCRIPTION OF THE PREFERRED EMBODIMENTS

Figure 1:
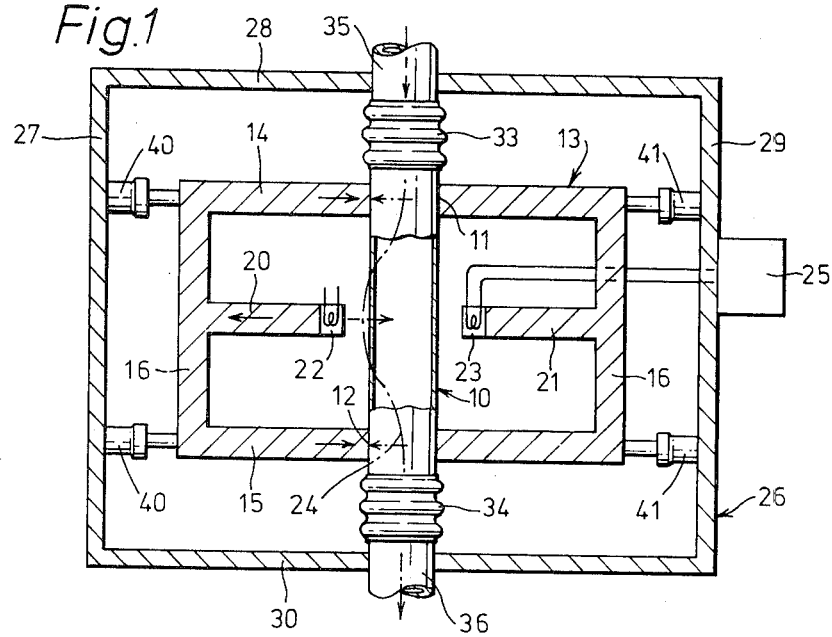
FIGS. 1 to 3 are diagrammatic cross-sectional views of three different embodiments of an apparatus according to the present invention for measuring the value of a fluid variable.

In FIG. 1 there is shown a first embodiment of an apparatus according to the present invention for measuring the value of the density of a fluid. The apparatus of FIG. 1 comprises a long, slender vibratory tube 10 which may be made of a magnetisable material, or of a non-magnetic material such as glass or stainless steel. Although the vibratory tube 10 would normally be cylindrical, this is not essential since the vibratory tube could, if desired, be square in cross-section, while its centre-line is not necessarily linear.

The vibratory tube 10 is rigidly fixed at nodes 11, 12 thereof to a holding structure 13 whose stiffness is at least 40% greater than that of the vibratory tube 10. Thus the stiffness of the holding structure 13 is preferably at least twice, and may be 10 times or more, that of the vibratory tube 10. This construction ensures that when, as described below, the vibratory tube 10 is set into vibration, it will vibrate in the clamped-clamped flexural mode of vibration.

The holding structure 13 comprises spaced apart frame members 14, 15 each of which is rigidly secured to the vibratory tube 10 at a respective node thereof. The frame members 14, 15 are rigidly interconnected by a plurality, e.g. two, tubular interconnecting members 16 each of which may consist if desired of one, two or more stiffening bars. The interconnector members 16 may either be rigidly secured to or may be integral with the frame members 14, 15. The stiffness of each of the interconnector members 16 is at least twice, and may be ten times or more, that of the vibratory tube 10.

The holding structure 13 also comprises arms 20, 21 which extend from respective interconnector members 16 and which respectively carry a driving coil 22 and a pick-up coil 23. The driving coil 22 and the pick-up coil 23 form part of a feedback oscillator (not shown) that maintains the vibratory tube 10 vibrating at its natural frequency. Although, for the sake of clarity, the driving coil 22 and pick-up coil 23 are shown as being well spaced from the vibratory tube 10, in practice the space therebetween is maintained as small as possible. Energisation of the driving coil 22 (by means not shown) causes the vibratory tube 10 to vibrate in the clamped-clamped flexural mode of vibration as indicated by the dotted line 24, such vibration being produced either by the direct magnetic effect on the vibratory tube 10, if the latter is made of a magnetisable material, or, by the magnetic effect on a magnetisable member carried by the vibratory tube 10, as described below.

Alternatively, the vibratory tube 10 may be excited mechanically (e.g. by piezo-electric or magnetostrictive means), acoustically (e.g. by the emission of a sound wave from a loudspeaker), or electrostatically.

The vibrations of the vibratory tube 10, which are affected by the density of the fluid passing through the latter, are sensed by the pick-up coil 23 from which signals are sent to a meter 25 which indicates the density of the fluid or which controls a process in dependence upon the value of such density.

The holding structure 13, and the vibratory tube 10 which is clamped within the latter, are mounted within a support 26 having wall members 27, 28, 29, 30. Opposite ends of the vibratory tube 10 are respectively connected by flexible bellows 33, 34 to tubes 35, 36 respectively which pass through the wall members 28, 30 respectively of the support 26.

Shock absorbers 40 are interposed between the wall member 27 of the support 26 and the frame members 14, 15 of the holding structure 13, while shock absorbers 41 are interposed between the frame members 14, 15 of the holding structure 13 and the wall member 29 of the support 26. The provision of the bellows 33, 34 and of the shock absorbers 40, 41 isolates the holding structure 13 from the support 26 in such a way as substantially to prevent transmission of vibration therebetween.

Thus, as will be appreciated, both the vibratory tube 10 and the holding structure 13 are connected to the support 26 by way of respective isolator means constituted by the bellows 33, 34 and shock absorbers 40, 41 respectively, the latter being disposed at right angles to the vibratory tube 10. The isolator means constituted by the bellows 33, 34 permit axial extension without compression of the vibratory tube 10, this being desirable since axial compression will increase the apparent density when the pressure of the fluid rises.

The construction shown in FIG. 1 has substantial advantages over the prior art. Since the vibratory tube 10 vibrates in the clamped-clamped flexural mode of vibration, the viscosity of the fluid passing through the vibratory tube 10 has very little damping effect on the vibration thereof. Moreover, the vibratory tube 10 may be constituted by a tube whose cross-sectional shape is not of importance and which therefore does not require any precision machining, nor matching with a similar tube, balancing weight, counter lever or the like.

Furthermore, the vibratory tube 10 can be made of materials such as stainless steel, glass, or ceramics, which normally cannot be employed in a density meter. In fact, the apparatus of the present invention can be made of dissimilar materials and yet can achieve an automatic temperature correction without the use of special materials such as that marketed under the Trade Mark "Ni-Span-C".

The holding structure 13 constitutes a stiff structure which defines the nodes of the clamped-clamped flexural mode of vibration, and the use of the holding structure 13, which is very simple to manufacture, thus avoids the need to use complicated constructions such as the twin tube construction and the cantilever/mass system described above to balance the reactions at the nodes. Since the holding structure 13 is substantially stiffer than the vibratory tube 10, only very small amplitude vibration will be transferred from the vibratory tube 10 to the holding structure 13.

In the construction shown in FIG. 1, moreover, both the driving coil 22 and the pick-up coil 23 are mounted on the arms 20, 21 respectively of the holding structure 13 and are thus mounted on the same stiff structure as holds the vibratory tube 10. This is an important feature of the present invention because it ensures that the whole system is balanced. Thus in accordance with Newton's Third Law, the driving force on the vibratory tube 10 has equal and opposite reactions on the driving means comprising the driving coil 22. Consequently, the reactions at the nodes 11, 12 are therefore balanced. Thus the construction shown in FIG. 1 permits the use of a single vibratory tube which is balanced in a particularly simple and therefore inexpensive way.

The provision of the bellows 33, 34 serves to isolate the vibratory tube 10 from any pipe-work carrying the fluid to be tested to and from the structure shown in FIG. 1, and thus prevents energy transmission therebetween. The vibratory tube 10 is also, in effect, isolated from the support 29 by the shock absorbers 40, 41 which act as anti-shock mountings so that plant vibrations will not affect its performance as a density meter.

Figure 2:
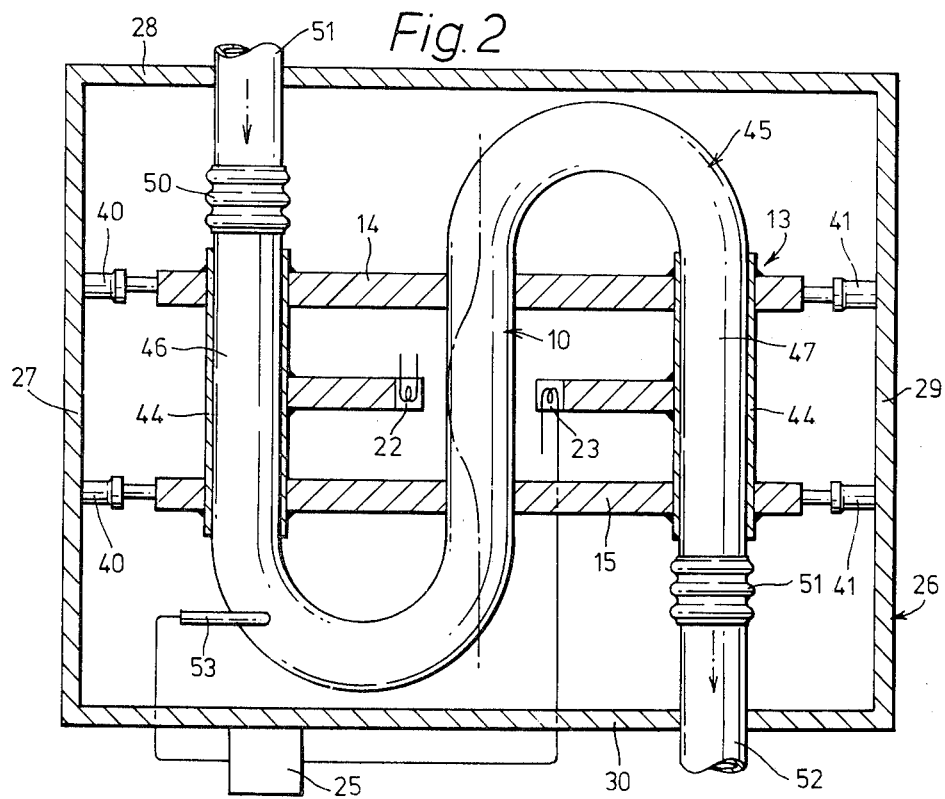

In FIG. 2 there is shown an apparatus which is generally similar to that of FIG. 1, and which for this reason will not be described in detail, like reference numerals indicating like parts.

In the FIG. 2 construction, however, the interconnector members 16 of the FIG. 1 construction are replaced by stiff tubular interconnector members 44 which are rigidly secured to the frame members 14, 15. Moreover, the vibratory tube 10 is constituted by one portion of a tube 45, the tube 45 having further portions 46, 47 each of which extends through and is in heat exchange relationship with a respective tubular interconnector member 44.

The tubular portion 46 is connected by means of a flexible bellows 50 to a tube 51 which passes through the wall member 28 of the support 26, while the tubular portion 47 is connected by a flexible bellows 51 to a tube 52 which passes through the wall member 30 of the support 26.

The construction shown in FIG. 2 serves to compensate for the effect of temperature on the value of the fluid density. Thus the arrangement is such as to pass the fluid, whose density is to be measured while it passes through the vibratory tube portion 10, in heat exchange relationship with the holding structure 13 so that there is substantially no temperature differential between the holding structure 13 and the vibratory tube 10. If temperature equalisation is not provided, the expansion of the vibratory tube 10 as the temperature rises relative to the stiff tubular interconnector members 44 will cause compressive stresses in the vibratory tube 10 with the result that the frequency of oscillation of the vibratory tube 10 will decrease. Also, the modulus of elasticity decreases with increase of temperature, which will in turn cause reduction in the frequency of oscillation of the tube and, if there were no temperature compensation, would cause an error in the density measurement.

The effect of the axial expansion is reduced by the construction shown in FIG. 2. Increases in the axial extension of the vibratory tube 10 are possible by means of the bellows 50, 51. However, if the tubular interconnector members 44 are at a different temperature than the vibratory tube 10, this will affect the change further.

In addition to the temperature equalisation achieved by passing the fluid through the tube portions 46, 47 in heat exchange relationship with the holding structure 13, or in substitution therefor, the temperature of the fluid which is about to pass through the vibratory tube 10, may be measured by at least one temperature-responsive member 53 (e.g. a P.R.T), both the pick-up coil 23 and the temperature responsive member 53 being connected to the meter 25 so that the reading of the latter will be adjusted in response to the temperature reading made by the temperature responsive member 53.

Alternatively, or additionally, the interconnector members 16 of the FIG. 1 construction, or the interconnector members 44 of the FIG. 2 construction, could be made of a material having a higher coefficient of thermal expansion than that of the vibratory tube 10 so that, on a rise in temperature, the consequent tensioning of the vibratory tube 10 compensates for the decrease in the modulus of elasticity of the tube material.

Thus temperature compensation could be effected by using stainless steel for the vibratory tube 10 and by using an aluminium alloy for the interconnector members 16.

Figure 3:
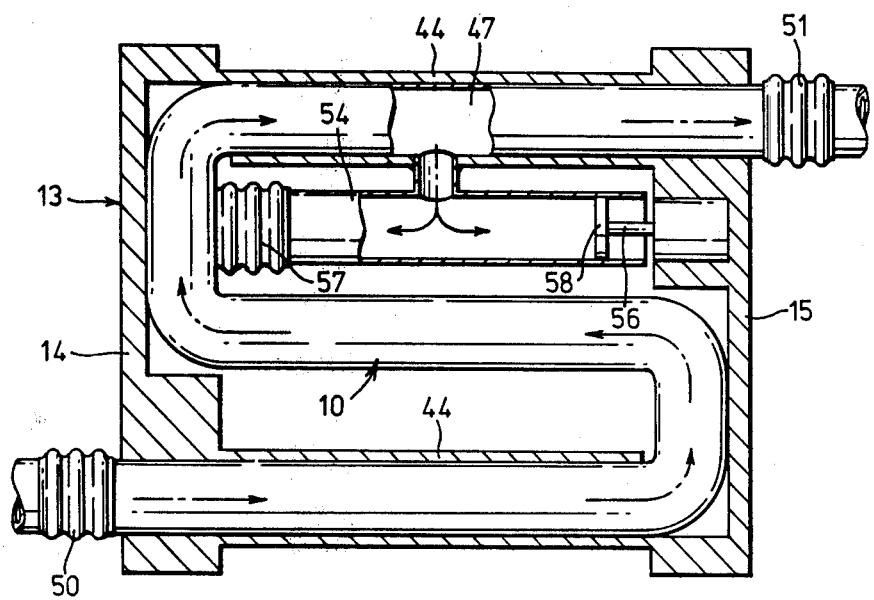

In FIG. 3 there is shown a further embodiment of the present invention which is generally similar to that of FIG. 2 and which for this reason will not be described in detail, like reference numerals indicating like parts.

In the FIG. 3 construction, however, a cylinder 54 which communicates with the tube portion 47, extends between the frame members 14, 15 and is connected thereto either by a piston and cylinder arrangement 56 or by a bellows 57. In order to reduce the number of drawings, FIG. 3 shows a piston and cylinder arrangement 56 on its right hand side and a bellows 57 on its left hand side. However, in practice, the apparatus would either be provided on its opposite sides with two piston and cylinder arrangements 56 or with two bellows 57.

In the case of the provision of the piston and cylinder arrangements 56, each of the frame members 14, 15 is connected to a piston 58 which is slidably mounted within the cylinder 54. Fluid passing through the vibratory tube 10 therefore acts on the head of the piston 58 so that the load on the latter, and therefore on the vibratory tube 10, depends upon the fluid pressure. Thus pressure compensation is achieved by applying a tensile stress to the vibratory tube 10 which varies with the pressure.

Similarly, in the case in which the bellows 57 are provided, a respective bellows 57 is provided between each of the frame members 14, 15 and the cylinder 54, the interior of each bellows 57 communicating with the interior of the vibratory tube 10. Thus the bellows 57 will compensate for the pressure effect.

If the vibratory tube 10 is subjected to increased internal pressure, it expands radially due to hoop stress, and contracts axially due to Poisson's Ratio. The resulting compression force decreases the frequency of vibration. However, the effects of such increased internal pressure on the frequency of vibration are reduced by the construction shown in FIG. 3 because the end loads which are imposed on the vibratory tube 10 by the piston and cylinder arrangements 56 or by the bellows 57 apply tensile stress to the vibratory tube 10. Thus as the pressure of the fluid in the vibratory tube 10 increases, so as to decrease the frequency of vibration thereof, the pressure of the fluid in the bellows 57 also increases, so as to increase the tensile stress imparted to the vibratory tube 10 and thus exercise a compensating effect.

A further method of achieving pressure compensation is to form the support 26 as a sealed enclosure within which the holding structure 13 and the vibratory tube 10 are mounted, and to subject both the interior and the exterior of the vibratory tube 10 to the pressure of the fluid whose density is to be measured.

Alternatively, if such a sealed enclosure is used, and the fluid is arranged to pass only through the interior of the vibratory tube 10, it is desirable to arrange either that this sealed enclosure contains dry air, so as to avoid condensation on the vibratory tube 10, or to arrange that the sealed enclosure is purged with an inert gas or is evacuated to give an absolute reference density.

Figure 4:
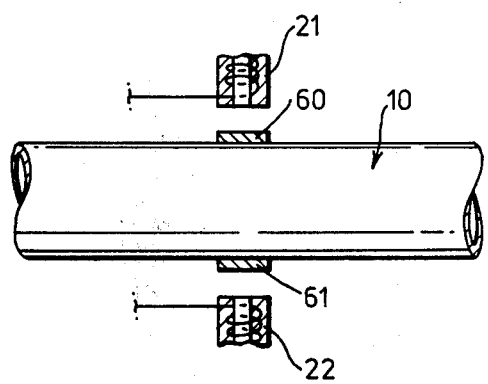
FIG. 4 is a broken-away cross-sectional view of a portion of an apparatus according to the present invention for measuring the value of a fluid variable.

In FIG. 4 there is shown part of an apparatus according to the present invention having a vibratory tube 10 made of a non-magnetic material such as stainless steel or glass. In order to enable the driving coil 22 to drive the vibratory tube 10, and the pick-up coil 21 to pick up the vibrations of the vibratory tube 10, the vibratory tube 10 is provided with two diametrically spaced apart magnetic washers or discs 60 which are disposed adjacent the coils 21, 22, or, alternatively, is provided with two diametrically spaced apart members 61, constituted by iron filings dispersed in epoxy resin material. In order to simplify the drawings, FIG. 4 shows the vibratory tube 10 as being provided with one washer 60 and one member 61.

If the vibratory tube 10 is made of stainless steel, the magnetic washer or discs 60 may be welded thereto, while if the vibratory member 10 is made of glass, the members 61 may be stuck thereto.

It will be appreciated from the above description that the apparatus of the present invention enables a wide range of different materials to be used in the making of the vibratory tube 10 and therefore allows the latter to be made of the materials suitable for use with corrosive fluid.

Although in the above description references have been made to an electro-magnetic driving system, the vibratory tube 10 may alternatively be driven by mechanical, pneumatic, acoustic, electrostatic, piezo-electric or magnetostrictive methods.

It is of course usual, in a context such as the present, to use electro-magnetic driving means, but this normally limits the applications of the apparatus to those which can employ a magnetic vibratory tube. In the case of the present invention, however, there is no such limitation.

The apparatus of the present invention does not suffer from hysteresis losses, and may easily be made in such a way as to be very easy to clean. Thus even in the construction shown in FIG. 2, the tube portions 10, 46, 47 could be made separable to permit cleaning.

The apparatus is suitable for use with fluids of all kinds including slurries (i.e. fluids containing solids), but it is specially useful in the case of very viscous fluids.

I claim:

1. Apparatus for measuring the value of a fluid variable comprising a vibratory tube through which the fluid may be passed; a holding structure rigidly fixing said vibratory tube at the nodes thereof for clamped-clamped flexural vibration, said holding structure having a stiffness at least 40% greater than that of the vibratory tube; driving means rigidly carried by said holding structure and arranged in operation to produce the said clamped-clamped flexural vibration of the vibratory tube; pick-up means rigidly carried by said holding structure and arranged in operation to respond to vibration of the vibratory tube; and a support which supports the holding structure and including isolator means which permit axial extension without compression of the vibratory tube.

2. Apparatus as claimed in claim 1 in which both the vibratory tube and the holding structure are connected to the said support by way of respective isolator means.

3. Apparatus as claimed in claim 1 in which there are tension producing means for producing axial tension of the vibratory tube.

4. Apparatus as claimed in claim 3 in which the tension producing means comprises a piston and cylinder arrangement, means being provided for supplying the cylinder with the said fluid.

5. Apparatus as claimed in claim 4 in which the piston is secured to the holding structure and is slidably mounted within a cylinder whose interior communicates with the interior of the vibratory tube.

6. Apparatus as claimed in claim 1 in which the isolator means comprises a bellows.

7. Apparatus as claimed in claim 6 comprising means for supplying the interior of the bellows with the said fluid.

8. Apparatus as claimed in claim 7 in which the bellows is interposed between the holding structure and the support, the interior of the bellows communicating with the interior of the vibratory tube.

9. Apparatus as claimed in claim 1 in which the isolator means comprise shock absorbers interposed between the holding structure and the support.

10. Apparatus as claimed in claim 1 in which the holding structure comprises two spaced frame members which are rigidly secured to the vibratory tube, and a plurality of interconnector members which extend between and are rigidly secured to or are integral with the frame members.

11. Apparatus as claimed in claim 10 in which the stiffness of each interconnector member is at least twice that of the vibratory tube.

12. Apparatus as claimed in claim 1 comprising compensating means which compensate for the effect of temperature on the value of the said fluid variable.

13. Apparatus as claimed in claim 12 in which the compensating means comprises means for passing the said fluid in heat exchange relationship with the holding structure so that there is substantially no temperature differential between the holding structure and the vibratory tube.

14. Apparatus as claimed in claim 10 or in claim 12 in which means are provided for passing said fluid in heat exchange relationship with said interconnector members.

15. Apparatus as claimed in claim 14 in which each interconnector member is a tubular member and the vibratory tube is constituted by one portion of a tube which is rigidly secured to and extends between the said frame members, the said tube having further portions thereof each of which extends through and is in heat exchange relationship with a respective tubular member.

16. Apparatus as claimed in claim 12 in which the compensating means comprises temperature responsive means for measuring the temperature of the fluid, the pick-up means being connected to a meter whose reading is adjusted by the temperature responsive means.

17. Apparatus as claimed in claim 10 or in claim 12 in which the interconnector members are made of a material having a higher coefficient of thermal expansion than that of the vibratory tube.

18. Apparatus as claimed in claim 1 comprising means for subjecting both the interior and the exterior of the vibratory tube to the pressure of the said fluid.

19. Apparatus as claimed in claim 1 in which the support comprises a sealed enclosure within which the holding structure and vibratory tube are mounted.

20. Apparatus as claimed in claim 19 in which the sealed enclosure contains dry air or an inert gas, or is evacuated.

21. Apparatus as claimed in claim 1 in which the driving means is an electromagnetic driving means and the vibratory tube, which is made of non-magnetic material, carries a magnetisable member disposed adjacent to the electromagnetic driving means.

22. Apparatus for measuring the value of a fluid variable comprising a vibratory tube through which the fluid may be passed; a holding structure mounting said vibratory tube for clamped-clamped flexural vibration, said holding structure having a stiffness at least 40% greater than that of the vibratory tube; driving means carried by said holding structure and arranged in operation to produce the said clamped-clamped flexural vibration of the vibratory tube; pick-up means arranged in operation to respond to vibration of the vibratory tube; and a support including respective isolator means for supporting the holding structure and vibratory tube while substantially preventing transmission of vibration between the support on the one hand and the holding structure and vibratory tube on the other hand.

23. Apparatus for measuring the value of a fluid variable comprising a vibratory tube through which the fluid may be passed; a holding structure mounting said vibratory tube for clamped-clamped flexural vibration, said holding structure having a stiffness at least 40% greater than that of the vibratory tube; driving means carried by said holding structure and arranged in operation to produce the said clamped-clamped flexural vibration of the vibratory tube; tension producing means for producing axial tension of the vibratory tube; pick-up means arranged in operation to respond to vibration of the vibratory tube; and a support which supports the holding structure and vibratory tube and including isolator means which substantially prevent transmission of vibration between the support on the one hand and the holding structure and vibratory tube on the other hand.

24. Apparatus for measuring the value of a fluid variable comprising a vibratory tube through which the fluid may be passed; a holding structure mounting said vibratory tube for clamped-clamped flexural vibration, said holding structure having a stiffness at least 40% greater than that of the vibratory tube; driving means carried by said holding structure and arranged in operation to produce the said clamped-clamped flexural vibration of the vibratory tube; a piston and cylinder arrangement for producing axial tension of the vibratory tube, the piston being secured to the holding structure and being slidably mounted in the cylinder, the cylinder interior communicating with the interior of the vibratory tube; means for supplying the fluid to the cylinder; pick-up means arranged in operation to respond to vibration of the vibratory tube; and a support supporting the holding structure and vibratory tube and including isolator means which substantially prevent transmission of vibration between the support on the one hand and the holding structure and vibratory tube on the other hand.

25. Apparatus for measuring the value of a fluid variable comprising a vibratory tube through which the fluid may be passed; a holding structure mounting said vibratory tube for clamped-clamped flexural vibration, said holding structure having a stiffness at least 40% greater than that of the vibratory tube; driving means carried by said holding structure and arranged in operation to produce the said clamped-clamped flexural vibration of the vibratory tube; pick-up means arranged in operation to respond to vibration of the vibratory tube; a support which supports the holding structure and vibratory tube and including isolator means which substantially prevent transmission of vibration between the support on the one hand and the holding structure and vibratory tube on the other hand, said isolator means comprising a bellows interposed between the holding structure and the support, the interior of the bellows communicating with the interior of the vibratory tube; and means for supplying the fluid to the interior of the bellows.

26. Apparatus for measuring the value of a fluid variable comprising a vibratory tube through which the fluid may be passed; a holding structure mounting said vibratory tube for clamped-clamped flexural vibration, said holding structure having a stiffness at least 40% greater than that of the vibratory tube; driving means carried by said holding structure and arranged in operation to produce the said claped-clamped flexural vibration of the vibratory tube; pick-up means arranged in operation to respond to vibration of the vibratory tube; temperature responsive means for measuring the temperature of the fluid; a meter connected to the pick-up means such that the reading of the meter is adjusted by the temperature responsive means in order to compensate for the effect of temperature on the value of said fluid variable; and a support which supports the holding structure and vibratory tube and which includes isolator means which substantially prevent transmission of vibration between the support on the one hand and the holding structure and vibratory tube on the other hand.

* * * * *